United States Patent
Boon-Falleur et al.

(10) Patent No.: US 6,221,593 B1
(45) Date of Patent: Apr. 24, 2001

(54) METHOD FOR DETERMINING CANCER BY DETERMINING EXPRESSION OF MAGE-10

(75) Inventors: Thierry Boon-Falleur; Francis Brasseur, both of Brussels (BE); Donata Rimoldi, Epalinges (CH); Etienne De Plaen, Brussels (BE)

(73) Assignee: Ludwig Institute for Cancer Research, England (GB)

( * ) Notice: Subject to any disclaimer, the term of this patent is extended or adjusted under 35 U.S.C. 154(b) by 0 days.

(21) Appl. No.: 09/183,714

(22) Filed: Oct. 30, 1998

Related U.S. Application Data

(63) Continuation-in-part of application No. 08/724,774, filed on Oct. 3, 1996, now Pat. No. 5,908,778.

(51) Int. Cl.⁷ .................................................... C12Q 1/68
(52) U.S. Cl. .............................................. 435/6; 536/23.1
(58) Field of Search ................................ 435/6; 536/23.1

(56) References Cited

U.S. PATENT DOCUMENTS 5,612,201    3/1997    DePlaen et al. .

FOREIGN PATENT DOCUMENTS

23874 * 9/1994 (WO) .
14463 * 4/1998 (WO) .

OTHER PUBLICATIONS

E. DePlaen, et al., Structure, Chromosomal Location, and Expression of 12 Genes of the MAGE Family, 1994, Immunogenetics vol. 40 p. 360.

S. Carrel, et al., Monoclonal Antibodies Against Recombinant–MAGE–1 Protein Identify A Cross Reacting 72–kDa Antigen Which Is co–Expressed With MAGE–1 Protein in Melanoma Cells, 1996, Int. J. Cancer, vol. 67 p. 417.

Bork, Genome Research vol. 10 p. 398, 2000.*

* cited by examiner

*Primary Examiner*—Sheela Huff
(74) *Attorney, Agent, or Firm*—Fulbright & Jaworski, LLP

(57) ABSTRACT

A correlation between expression of tumor rejection antigen precursor MAGE-10 and cancer has been discovered. The invention is a method for determining presence of cancer in a sample by determining expression of MAGE-10. This determination can be made via, e.g., an immunoassay, an oligonucleotide hybridization assay, or via other standard methodologies.

9 Claims, 2 Drawing Sheets

SEQUENCE LISTING

```
<160> NUMBER OF SEQ ID NOS: 7

<210> SEQ ID NO: 1
<211> LENGTH: 19
<212> TYPE: DNA
<213> ORGANISM: Homo sapiens
<220> FEATURE:

<400> SEQUENCE: 1
gtggcgacga ctcctggag                                              19

<210> SEQ ID NO: 2
<211> LENGTH: 23
<212> TYPE: DNA
<213> ORGANISM: Homo sapiens
<220> FEATURE:

<400> SEQUENCE: 2
cagaccaact ggtaatggta gcg                                         23

<210> SEQ ID NO: 3
<211> LENGTH: 2559
<212> TYPE: DNA
<213> ORGANISM: Homo sapiens
<220> FEATURE:

<400> SEQUENCE: 3
tccggggtcg ctcgagccgg ccgggactcg gggatcasaa gtaacggcgg            50
yymkygtkct gagggacagg cttgagatcg gctgaagaga gcgggcccag            100
gctctgtgag gaggcaaggg aggtgagaac cttgctctca gagggtgact            150
caagtcaaca cagggaaccc ctcttttcta cagacacagt gggtcgcagg            200
```

-continued

| | |
|---|---|
| atctgacaag agtccaggtt ctcaggggac agggagagca agaggtcaag | 250 |
| agctgtggga caccacagag cagcactgaa ggagaagacc tgcctgtggg | 300 |
| tccccatcgc ccaagtcctg cccacactcc cacctgctac cctgatcaga | 350 |
| gtcatcatgc ctcgagctcc aaagcgtcag cgctgcatgc ctgaagaaga | 400 |
| tcttcaatcc caaagtgaga cacagggcct cgagggtgca caggctcccc | 450 |
| tggctgtgga ggaggatgct tcatcatcca cttccaccag ctcctctttt | 500 |
| ccatcctctt ttccctcctc ctcctcttcc tcctcctcct cctgctatcc | 550 |
| tctaatacca agcaccccag aggaggtttc tgctgatgat gagacaccaa | 600 |
| atcctcccca gagtgctcag atagcctgct cctcccctc ggtcgttgct | 650 |
| tcccttccat tagatcaatc tgatgagggc tccagcagcc aaaaggagga | 700 |
| gagtccaagc accctacagg tcctgccaga cagtgagtct ttacccagaa | 750 |
| gtgagataga tgaaaaggtg actgatttgg tgcagtttct gctcttcaag | 800 |
| tatcaaatga aggagccgat cacaaaggca gaaatactgg agagtgtcat | 850 |
| aaaaaattat gaagaccact tccctttgtt gtttagtgaa gcctccgagt | 900 |
| gcatgctgct ggtctttggc attgatgtaa aggaagtgga tcccactggc | 950 |
| cactcctttg tccttgtcac ctccctgggc ctcacctatg atgggatgct | 1000 |
| gagtgatgtc cagagcatgc ccaagactgg cattctcata cttatcctaa | 1050 |
| gcataatctt catagagggc tactgcaccc ctgaggaggt catctgggaa | 1100 |
| gcactgaata tgatgggggct gtatgatggg atggagcacc tcatttatgg | 1150 |
| ggagcccagg aagctgctca cccaagattg ggtgcaggaa aactacctgg | 1200 |
| agtaccggca ggtgcctggc agtgatcctg cacggtatga gtttctgtgg | 1250 |
| ggtccaaggg ctcatgctga aattaggaag atgagtctcc tgaaatttt | 1300 |
| ggccaaggta aatgggagtg atccaagatc cttcccactg tggtatgagg | 1350 |
| aggctttgaa agatgaggaa gagagagccc aggacagaat tgccaccaca | 1400 |
| gatgatacta ctgccatggc cagtgcaagt tctagcgcta caggtagctt | 1450 |
| ctcctacccct gaataaagta agacagattc ttcactgtgt tttaaaaggc | 1500 |
| aagtcaaata ccacatgatt ttactcatat gtggaatcta aaaaaaaaaa | 1550 |
| aaaaaaaagt tggtatcatg gaagtagaga gtagagcagt agttacatta | 1600 |
| caattaaata ggaggaataa gttctagtgt tctattgcac agtaggatga | 1650 |
| ctatagttaa cattaagata ttgtatatta caaaacagct agaaggaagg | 1700 |
| cttttcaata ttgtcaccaa aaagaaatga taaatgcatg aggtgatgga | 1750 |
| tacactacct gatgtgatca ttatactaca tatacatgaa tcagaacatc | 1800 |
| aaattgtacc tcataaatat ctacaattac atgtcagttt ttgtttatgt | 1850 |
| ttttgttttt ttttaattta tgaaaacaaa tgagaatgga aatcaatgat | 1900 |
| gtatgtggtg gagggccagg ctgaggctga ggaaaataca gtgcataaca | 1950 |
| tctttgtctt actgtttct ttggataacc tggggacttc ttttcttttc | 2000 |
| ttcttggtat tttattttct ttttcttctt cttcttttt ttttttaaca | 2050 |
| aagtctcact ctattgctct ggcaggagtg cagtggtgca gtctcggctc | 2100 |
| actgcaactt ccgcctcctg ggttcaagcg attctcctgc ctcagtctcc | 2150 |
| tgagtagctg ggattacaag tgtgcaccac cataccggc taattttgta | 2200 |

```
ttttttagta gagatggggt ttcaccatgt tggccaggct ggtctcaaac      2250
tcctgacctc aggtaatctg cccgcctcag cctcccaaag tgctgggata      2300
acaggtgtga gcccactgca ccccagcctc ttcttggtat tttaaaatgt      2350
tgttactttt actagaatgt ttatgagctt cagaatctaa ggtcacacgt      2400
tcgtttctgt ttatccagtt taagaaacag ttttgctatt ttgtaaaaca      2450
aattgggaac ccttccatca tatttgtaat ctttaataaa ataacatgga      2500
attggaatag taattttctt ggaaatatga aaaaatagta aatagagaa       2550 aataatttt                                                   2559
```

<210> SEQ ID NO: 4
<211> LENGTH: 28
<212> TYPE: PRT
<213> ORGANISM: Homo sapiens
<220> FEATURE:

<400> SEQUENCE: 4

Gln Asp Arg Ile Ala Thr Thr Asp Asp Thr
 1               5                  10

Thr Ala Met ala Ser Ala Ser Ser Ser Ala
                15                  20

Thr Gly Ser Phe Ser Tyr Pro Glu
                25          28

<210> SEQ ID NO: 5
<211> LENGTH: 21
<212> TYPE: PRT
<213> ORGANISM: Homo sapiens
<220> FEATURE:

<400> SEQUENCE: 5

Phe Asn Asn Phe Thr Val Ser Phe Trp Leu
 1               5                  10

Arg Val Pro Lys Val Ser Ala Ser His Leu Glu
                15                  20

<210> SEQ ID NO: 6
<211> LENGTH: 21
<212> TYPE: DNA
<213> ORGANISM: Homo sapiens
<220> FEATURE:

<400> SEQUENCE: 6
cacagagcag cactgaagga g                                     21

<210> SEQ ID NO: 7
<211> LENGTH: 23
<212> TYPE: DNA
<213> ORGANISM: Homo sapiens
<220> FEATURE:

<400> SEQUENCE: 7
ctgggtaaag actcactgtc tgg                                   23

METHOD FOR DETERMINING CANCER BY DETERMINING EXPRESSION OF MAGE-10

RELATED APPLICATION

This application is a continuation in part of Ser. No. 08/724,774 filed Oct. 3, 1996, now U.S. Pat. No. 5,908,778, and incorporated by reference.

FIELD OF THE INVENTION

This invention relates to tumor rejection antigen precursors, the nucleic acid molecules encoding them, antibodies specific to these, and uses thereof.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum antigens are obtained by mutating tumor cells which do not generate an immune response in syngeneic mice and will form tumors (i.e., "tum$^+$" cells). When these tum$^+$ cells are mutagenized, they are rejected by syngeneic mice, and fail to form tumors (thus "tum"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum variants fail to form progressive tumors because they initiate an immune rejection process. The evidence in favor of this hypothesis includes the ability of "tum$^-$" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum$^-$ cells of mastocytoma P815 multiply exponentially for 12–15 days, and then are eliminated in only a few days in the midst of an influx of lymphocytes and macrophages (Uyttenhove et al., J. Exp.

Med. 152: 1175–1183 (1980)). Further evidence includes the observation that mice acquire an immune memory which permits them to resist subsequent challenge to the same tum$^-$ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the tumor rejection antigens are lysed. Characterization studies have identified CTL clones which specifically lyse cells expressing the tumor rejection antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum–" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum variants following mutagenesis, including variants referred to as P91A (DePlaen, supra), 35B (Szikora, supra), and P198 (Sibille, supra). In contrast to tumor rejection antigens—and this is a key distinction—the tum$^-$ antigens are only present after the tumor cells are mutagenized. Tumor rejection antigens are present on cells of a given tumor without mutagenesis. Hence, with reference to the literature, a cell line can be tum$^+$, such as the line referred to as "P1", and can be provoked to produce tum variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991) and De Plaen, et al., Immunogenetics 40: 360 (1994).

U.S. Pat. No. 5,342,774, cited supra and incorporated by reference, teaches various members of the MAGE family of TRAPs, in genomic DNA and cDNA form. Genomic DNA for MAGE-10 is taught in PCT application PCT/US92/04354, cited supra, in SEQ ID NO: 22, as a 920 base pair fragment. DePlaen, et al., Immunogenetics 40: 360–369 (1994), discusses PCR work which identified a 485 nucleotide portion of MAGE-10. Also, see Genbank Accession No. U10685, incorporated by reference. A cDNA molecule, however, is not discussed.

The previously cited PCT application discusses antibodies to MAGE proteins generally. Chen et al., U.S. Pat. No. 5,541,104, to Chen et al., incorporated by reference, teaches monoclonal antibodies which specifically bind to tumor rejection antigen precursor MAGE-1. This patent is incorporated by reference. In order to prepare the monoclonal antibodies, Chen et al produced a MAGE-1 TRAP in E. coli which was not full length, because of difficulties with expression of the full length molecule.

It has now been found, however, that monoclonal antibodies which bind to both MAGE-1 and MAGE-10 TRAP can be produced. This is surprising in view of the reports in the literature, because it was not seen to be possible to produce such antibodies with the available information on MAGE-10. The TRAP encoded by the cDNA for MAGE-10 is found to be a molecule of about 72 kilodaltons molecular weight, on SDS-PAGE. It has also been found that polyclonal antibodies specific to MAGE-10 can be produced. It has also been found that expression of MAGE-10 can be expressly linked to presence of cancer in a sample. U.S. Pat. No. 5,612,201 reported weak expression of MAGE 5 and 8–11 in all tissues tested, and did not correlate expression of MAGE-10 to any cancers whatsoever. It has now been found, however, that MAGE-10 can be so linked. Hence, the determination of cancer in a sample by determining expression of MAGE-10 is yet a further feature of this invention.

DETAILED DESCRIPTION OF PREFERRED EMBODIMENTS

EXAMPLE 1

Figure 1:
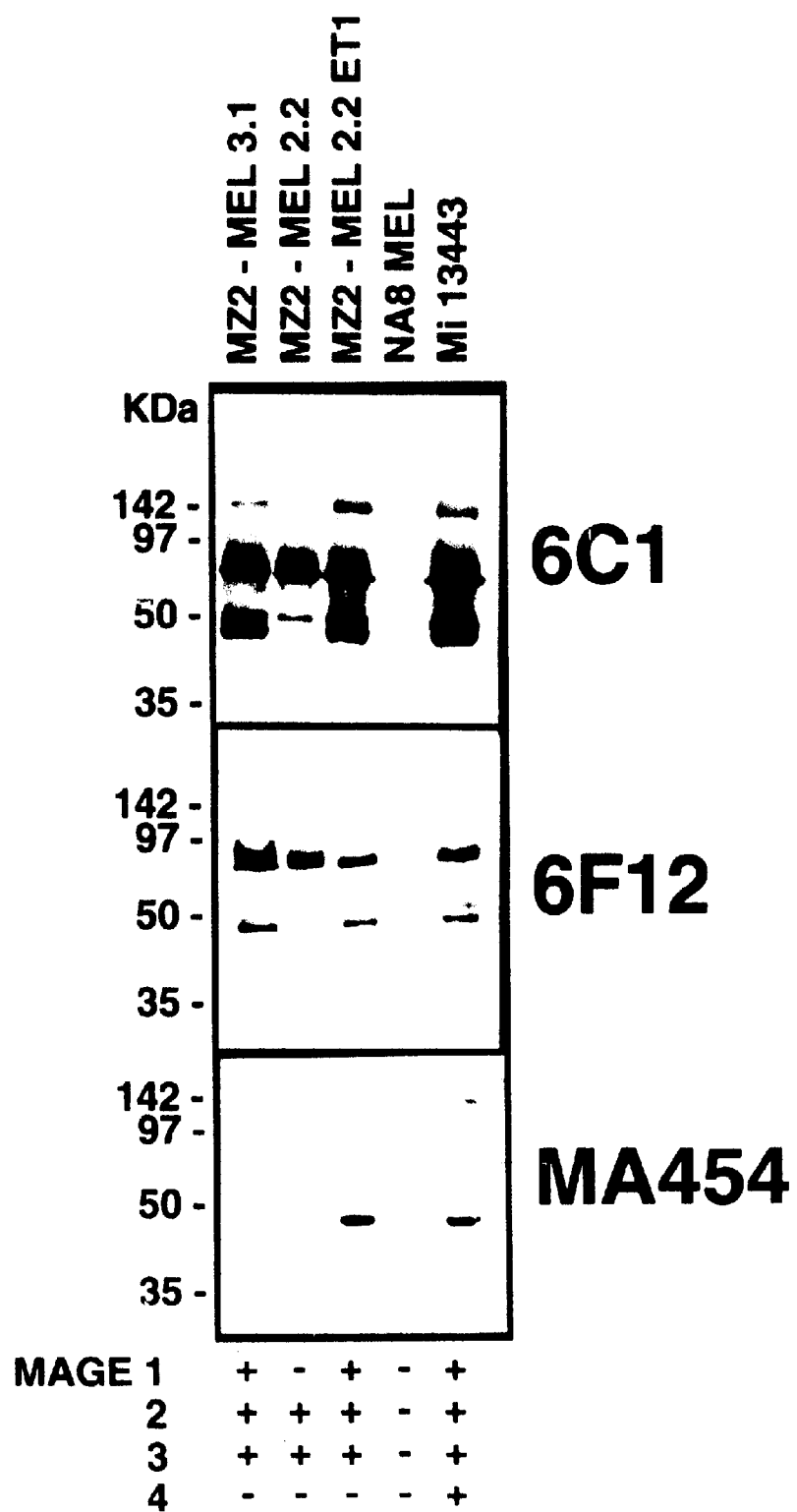
FIG. 1 presents results of a Western blotting assay, using electrochemiluminescence detection to test reactivity of monoclonal antibodies with various cell lysates.

Full length recombinant MAGE-1 protein was prepared in the form of a fusion protein, in E. coli. See Schultz-Thater, et al., Int. J. Cancer 59: 435–439 (1994), incorporated by reference. Briefly, full length MAGE-1 cDNA was cloned into a well known expression vector, pET 16b. This vector permits expression of a fusion protein which contains 10 histidine molecules at the N-terminus. The E. coli were cultured, following Schultz-Thater, after which the cells were lysed, and the recombinant fusion protein was purified on a $Ni^{2+}$ column. The purified material, when tested by SDS-PAGE, showed a major band of 48 kilodaltons. This 48 kD material was used in the experiments which follow.

EXAMPLE 2

Following the production of the recombinant MAGE-1 fusion protein, a BALB/c mouse was immunized intraperitoneally, twice, with 20 ug of the recombinant protein each time, in a composition which contained complete Freund's adjuvant. This was followed by two additional injections, each of 20 ug of recombinant MAGE-1, with incomplete Freund's adjuvant. The spleen cells of the mouse were then fused with NS-1 myeloma cells, in accordance with Carrel, et al., Cancer Res. 40: 2523–2528 (1980). The resulting hybridoma cells were cultured, and supernatants from the cultures were screened, using an ELISA, to determine if recombinant MAGE-1 specific monoclonal antibodies were being produced. The ELISA involved coating recombinant MAGE-1 protein (250 ng/50 ul per well), followed by overnight incubation at 4° C. Samples of supernatant were added, followed by biotin conjugated sheep antimouse Ig, and streptavidin-alkaline phosphatase conjugate.

The ELISA resulted in the identification of 289 hybridomas which produced antibodies against recombinant MAGE-1.

EXAMPLE 3

In the next set of experiments, the antibodies were tested to determine if they could be used to immunostain cells which were positive for mRNA for MAGE-1.

Initially the hybridomas were screened to try to eliminate any cross reactive monoclonals. To do this, cell lines with known, and different patterns of MAGE-TRAP expression were tested. MZ2-MEL 3.1 is known to express all of MAGE-1, 2, 3 and 4; MZ2-MEL 2.2 expresses MAGE-2 and 3; and U251, a glioblastoma cell line negative for all four, were tested. Cells were cultured in 16 well plastic chambers, fixed in cold acetone (0° C. for five minutes), and then stored until ready to use at −20° C. Endogenous peroxidase was then blocked with 0.3% $H_2O_2$ (10 minutes), and the cells were then preincubated, in 0.1% bovine serum albumin in phosphate buffered saline, for 30 minutes. This produced a first layer of a three layer biotin/avidin/peroxidase system as described by Carrel, et al., supra. Following the fixing of the cells, goat anti-mouse IgG biotin conjugate was added (following 1:50 dilution), to yield the second layer. Finally, avidin-peroxidase conjugates were added, following dilution at 1:1000. In the case of the second and third layers, incubation was for 30 minutes and then 15 minutes. Peroxidase was visualized with amino-ethylcarbazole, and counter staining of cells, using Gill's hematoxylin for 30 seconds. This set of experiments results in the discovery that two mAbs, i.e., 6C1 and 6F2, stained only the MZ2-MEL 3.1 cells. These two clones were then used in a series of experiments on cells which had been tested for mRNA for MAGE-1, 2, 3 and 4. Cells were classified as being positive or negative for MAGE-1 mRNA expression. This was determined by following the procedures of Rimoldi et al., Int. J. Cancer 54: 527–528 (1993); Brasseur et al., Int. J. Cancer 63: 375–380 (1995). In brief, total RNA was extracted from cell samples using well known, commercially available methods and reagents, and then subjected to reverse transcription and polymerase chain reaction using MAGE-1, MAGE-2, MAGE-3 and MAGE-4 specific primers. See Brasseur. et al. supra. Table 1, which follows, presents the results of this work. It shows that, regardless of status of MAGE-2, 3 or 4 expression both mAbs stained all MAGE-1 positive cells.

TABLE I

IMMUNOCYTOCHEMICAL REACTIVITY OF
MAbs 6Cl AND 6F12 WITH VARIOUS CELL LINES

| Cell lines | Immunostaining[1] | | MAGE-mRNA expression[2] |
|---|---|---|---|
| | MAb 6Cl | MAb 6F12 | |
| [a]MZ2-MEL 3.1 | + | + | $1^\oplus, 2^\oplus, 3^\oplus, 4^\oplus$ |
| [a]MZ2-MEL 2.2 | − | − | $1^-, 2^\oplus, 3^\oplus, 4^-$ |
| [a]MZ2-MEL 2.2 ET1 | + | + | $1^\oplus, 2^\oplus, 3^\oplus, 4^-$ |
| [a]Me235 | + | + | $1^\oplus, 2^\oplus, 3^\oplus, 4^-$ |
| [a]Mi13443 | + | + | $1^\oplus, 2^\oplus, 3^\oplus, 4^\oplus$ |
| [a]NA8-MEL | − | − | $1^-, 2^-, 3^-, 4^-$ |
| [a]Me220 | − | − | $1^-, 2^-, 3^-, 4^-$ |
| [a]Me241-2 | + | + | $1^\oplus, 2^-, 3^-, 4^-$ |
| [a]Mi9 | − | − | $1^-, 2^\oplus, 3^\oplus, 4^-$ |
| [a]Mi13 | − | − | $1^-, 2^\oplus, 3^\oplus, 4^-$ |
| [a]Mi21 | − | − | $1^-, 2^-, 3^\oplus, 4^-$ |
| [b]U251 | − | − | $1^-, 2^-, 3^-, 4^-$ |
| [c]MCF7 | − | − | $1^-, 2^-, 3^-, 4^-$ |
| [d]FeK4 | − | − | $1^-, 2^-, 3^-, 4^-$ |
| [e]P815 | − | − | $1^-, 2^-, 3^-, 4^-$ |
| [f]P815/MAGE-1 | + | + | $1^\oplus, 2^-, 3, 4^-$ |
| [g]HEL | + | + | $1^\oplus, 2^-, 3^-, 4^-$ |
| [g]TF1 | − | − | $1^-, 2^-, 3^\oplus, 4^-$ |

[a]Melanoma; [b]glioblastoma; [c]breast carcinoma; [d]fibroblast; [e]mouse mastocytoma; [f]mouse mastocytoma transfected with MAGE-1 cDNA; [g]myeloid leukemia.—[1]Acetone-fixed cells were stained by a 3-layer biotin/avidin/peroxidase system.—[2]The cellular mRNA was reverse transcribed and the cDNA tested by PCR using primers specific for MAGE-1, -2, -3 or -4 sequences.

EXAMPLE 4

A further set of experiments were then carried out, using the well known Western blotting technique. Five cell lines were tested, i.e., MZ2-MEL 3.1, MZ2-MEL 2.2, MZ2-MEL 2.2 ET1, NA8 MEL, and Mi13443. All of these lines are presented in Table 1, supra. Cells were cultured, and then lysed in a Nonidet P40 (NP-40) buffer (150 mM NaCl, 0.5% NP-40, 2 mM EDTA, 80 mM Tris-HCl, pH 7.5, 0.02% NaN$_3$, 100 ug/ml PMSF and 100 ug/ml aprotinin). Approximately 50 ug aliquots were then subjected to SDS-PAGE under reducing conditions, and the thus separated proteins were transferred to nitrocellulose paper. Undiluted hybridoma supernatants, and a standard, commercially available electrochemiluminescence detection system was used. FIG. 1 shows these results. They were intriguing because two major bands were found by both mAbs when testing MZ2-MEL 3.1. These bands are at 46 and 72 kilodaltons. The known MAGE-1 specific monoclonal antibody MA454 (Chen, et al., Proc. Natl. Acad. Sci. USA 91: 1004–1008 (1994); U.S. Pat. No. 5,541,104)) did not detect anything in MAGE-1 negative cell line MZ2-MEL 2.2, but when this cell line was transfected with MAGE-1 cDNA (to become cell line MZ2-MEL 2.2 ET1), MA 454 mAb did bind to a 46 kD band. One concludes from this that the 46 kilodalton species bound by all of MA454, 6C1, and 6F12, is MAGE-1 protein, but that the latter two mAbs are cross reactive with a second, 72 kilodaltons protein which was expressed by MZ2-MEL 3.1, MZ2-MEL 2.2, and Mi13443 (as well as transfected MZ2 MEL 2.2. ET1). Note, however, that MZ2-MEL 2.2 is MAGE-1 negative, suggesting that the cross reactivity is with a non-MAGE-1 protein.

EXAMPLE 5

Figure 2:
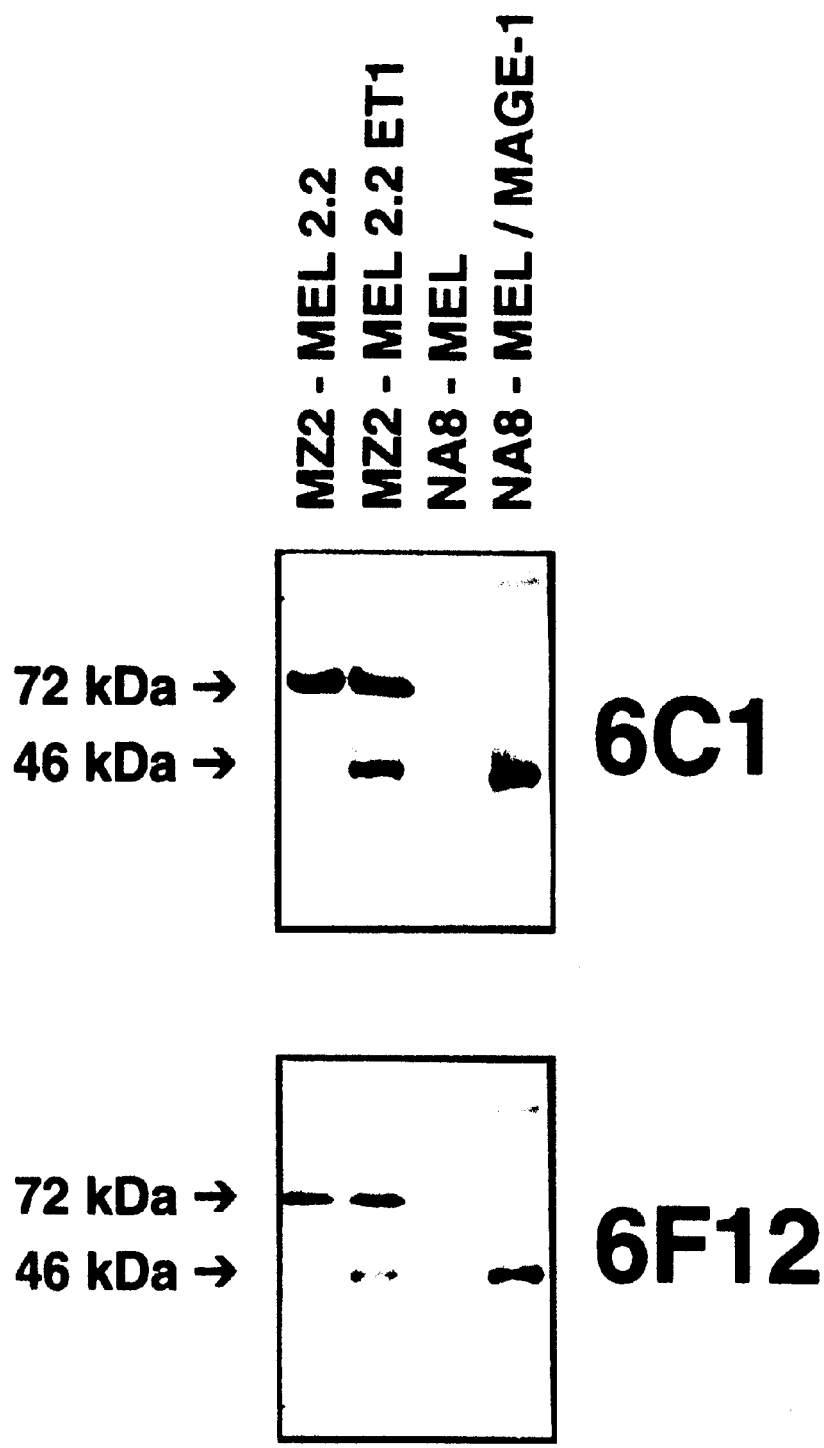
FIG. 2 presents results of tests designed to determine if cell line NA8-MEL could be induced to produce 72 kilodalton protein in the presence of MAGE-1 cDNA.

The fact that NA8-MEL did not express any of MAGE-1, 2, 3 or 4 and did not produce any proteins which bound to any of the three mAbs tested, made it useful in experiments to determine whether or not detection of the 72 kDa protein was dependent on presence of MAGE-1. The NA8-MEL cells were transiently transfected with MAGE-1 cDNA in plasmid pcDNAI, using lipofectin. The transfected cells were lysed, and analyzed via Western blotting, as described supra, using 6C1 and 6F12. A band of 46 kilodaltons resulted, as did a faint band corresponding to what is believed to be a multimeric form of MAGE-1. See FIG. 2. No 72 kDa band was found, however. There was no 72 kDa protein found following transient transfection with each of MAGE-2, 3, 4 and 12. This was also true with COS-7 cells, following transient transfection.

EXAMPLE 6

In view of the unexpected presence of the 72 kDalton band, Western blotting was carried out in accordance with the procedures set forth supra, on a large number of cells. The results are shown in Table 2, which also presents results from MAGE-1, 2, 3 and 4 mRNA 15i expression testing. There was no relationship observed between the 46 and 72 kDalton proteins.

TABLE II

DETECTION OF MAGE-1 PROTEIN AND
THE 72-kDa PROTEIN IN CELL LINES BY
WESTERN BLOTTING WITH MAbs 6Cl and 6F12

| Cell lines | Western blot | | MAGE-mRNA expression |
|---|---|---|---|
| | MAGE-1 protein | 72-kDa protein | |
| [a]MZ2-MEL 3.1 | + | + | $1^\oplus, 2^\oplus, 3^\oplus, 4^\oplus$ |
| [a]MZ2-MEL 2.2 | − | + | $1^-, 2^\oplus, 3^\oplus, 4^-$ |
| [a]MZ2-MEL 2.2 ET1 | + | + | $1^\oplus, 2^\oplus, 3^\oplus, 4^-$ |
| [a]Mi13443 | + | + | $1^\oplus, 2^\oplus, 3^\oplus, 4^\oplus$ |
| [a]NA8-MEL | − | − | $1^-, 2^-, 3^-, 4^-$ |
| [a]IGR39 | − | − | $1^-, 2^-, 3^-, 4^-$ |
| [a]Me272.LN2 | − | − | $1^-, 2^-, 3^\oplus, 4^-$ |
| [a]Me220 | − | − | $1^-, 2^-, 3^-, 4^-$ |
| [a]IGR3 | + | + | $1^\oplus, 2^\oplus, 3^\oplus, 4^\oplus$ |
| [a]Me204.A.1 | − | − | $1^-, 2^\oplus, 3^\oplus, 4^-$ |
| [a]Me242.B.1 | − | − | $1^-, 2^\oplus, 3^-, 4^-$ |
| [a]Me241.1 | + | + | $1^\oplus, 2^-, 3^\oplus, 4^-$ |
| [a]Me235 | + | + | $1^\oplus, 2^\oplus, 3^\oplus, 4^-$ |
| [a]Me192.2.20 | + | + | $1^\oplus, 2^\oplus, 3^\oplus, 4^\oplus$ |
| [a]Mi9 | − | − | $1^-, 2^\oplus, 3^\oplus, 4^-$ |
| [a]Mi13 | − | − | $1^-, 2^\oplus, 3^\oplus, 4$ |
| [a]Mi21 | − | − | $1^-, 2^-, 3^\oplus, 4^-$ |
| [a]Me248.3 | + | + | $1^\oplus, 2^\oplus, 3^\oplus, 4^\oplus$ |

TABLE II-continued

DETECTION OF MAGE-1 PROTEIN AND
THE 72-kDa PROTEIN IN CELL LINES BY
WESTERN BLOTTING WITH MAbs 6C1 and 6F12

| Cell lines | Western blot | | MAGE-mRNA expression |
|---|---|---|---|
| | MAGE-1 protein | 72-kDa protein | |
| (a)Me244.1 | + | + | $1^\oplus, 2^\oplus, 3^-, 4^-$ |
| (a)Me222.6 | + | + | $1^\oplus, 2^\oplus, 3^\oplus, 4^-$ |
| (a)M14 | + | + | $1^\oplus, 2^\oplus, 3^\oplus, 4^\oplus$ |
| (b)Cl-18 | + | − | $1^\oplus, 2^-, 3^\oplus, 4^-$ |
| (b)U251 | − | − | $1^-, 2^-, 3^-, 4^-$ |
| (b)LN215 | + | + | $1^\oplus, 2^\oplus, 3^\oplus, 4^-$ |
| (c)TF1 | − | − | $1^-, 2^-, 3^\oplus, 4^-$ |
| (c)HEL | + | − | $1^\oplus, 2^-, 3^-, 4^-$ |
| (d)MC17 | − | − | $1^-, 2^-, 3^-, 4^-$ |
| (e)ACN | + | − | $1^\oplus, 2^\oplus, 3^\oplus, 4$ |
| (e)LAN-2 | + | + | $1^\oplus, 2^\oplus, 3^\oplus, 4^\oplus$ |
| (f)Fek4 | − | − | $1^-, 2^-, 3^-, 4^-$ |

(a)Melanoma; (b)glioblastoma; (c)myeloid leukemia; (d)breast carcinoma; (e)neuroblastoma; (f)fibroblast.

EXAMPLE 7

It is known that MAGE-1 expression can be induced, in vitro, in some MAGE-1 mRNA negative cell lines, by 5-aza-2'-deoxycytidine, a hypomethylating agent("DAC"). This agent was incubated with three MAGE-1 mRNA negative cell lines (IGR 39, NA8-MEL, and U251), for 72 hours, after which lysates were taken, and incubated with monoclonal antibody 6C1. This treatment induced production of both the 46 kDa and the 72 kDa protein.

EXAMPLE 8

The intriguing results reported supra suggested further experiments to determine the identity of the 72 kDa protein. First, a melanoma expression library was prepared from melanoma cell line MZ2-MEL 43, using a commercially available system. Following the preparation, bacteriophages were plated (approximately 4×10⁵ pfus), and transferred to nitrocellulose filters. These were then blocked with 5% milk powder in phosphate buffered saline, and then incubated with monoclonal antibody 6C1 (hybridoma supernatant diluted 1:4 in RPMI/10% fetal calf serum). The materials were then washed with PBS/0.5% Tween-20 and incubated with horseradish peroxidase conjugated sheep anti-mouse IgG, diluted 1:3000 in PBS/5% milk powder in PBS. Another wash, with 5% Tween-20 followed. Signals were detected using ECL, as discussed supra. All positive plaques were subjected to secondary and tertiary screening. Positives were then picked and transferred to a tube containing phage lysis buffer (20 mM Tris-HCl, pH 8.3, 50 mM KCl, 0.1% Tween 20), and an aliquot of this (5 ul) was used to amplify phage inserts.

These were amplified via PCR, using:

GTGGCGACGA CTCCTGGAG (SEQ ID NO: 1) and

CAGACCAACT GGTAATGGTA GCG (SEQ ID NO: 2)

which are λ primers. The cycling parameters were: 1 minute at 94° C., 1 minute at 61° C., and 1 minute at 72° C., for 30 cycles, followed by a final extension at 72° C., for 10 minutes.

A partial 5' sequence of the clones was then obtained, using a commercially available sequencing kit, using SEQ ID NO: 1. See Casanova, Meth. Mol. Biol. 23: 191–197 (1993). Twelve clones were sequenced, and three were found to be identical to that of the MAGE-10 genomic sequence, as reported by DePlaen et al., Immunogenetics 40: 360–369 (1994), and Genbank Accession No. U10685.

One insert was then amplified, using SEQ ID NOS: 1 and 2, and a commercially available system. The cycling parameters for this amplification were 15 seconds at 94° C., 30 seconds at 61° C., 1 minute at 72° C. (10 cycles), 15 seconds at 94° C., 30 seconds at 61 ° C., 80 seconds plus 20 seconds cycle elongation at 72° C., for 20 cycles followed by 10 minutes at 72° C., for a final extension. The amplification product was cleaved with restriction endonucleases NotI and SalI, and then subcloned into Bluescript plasmid. Automated sequencing was then carried out using T3 and T7 primers. It was confirmed to be a partial MAGE-10 cDNA sequence (1400 base pairs), which corresponded to a start at position 2770 at the 5'-end, and extending 660 base pairs beyond the 3'-end of the genomic sequence reported by DePlaen, et al., supra.

EXAMPLE 9

Using the information obtained from the experiments described, supra, additional work was carried out to obtain a full length cDNA clone for MAGE-10.

As indicated, the partial cDNA clone was 1.4 kb long. This fragment was subjected to digestion with restriction endonucleases, and an HpaI fragment, corresponding to nucleotides 2770–3510 of the known, gDNA sequence, was isolated, and $^{32}P$ labeled, using a random priming DNA labeling kit. The labeled probe was then used to screen two libraries from a melanoma cell line LB73-MEL, in the vectors pcDNAI/Amp and pCEP4. The hybridization was carried out on filters, using 5×SSC, 5×Denhardt's, 0.5% SDS, and 100 ug/ml denatured salmon sperm DNA, at 65° C. Filters were then washed three times for 10 minutes at room temperature, with 1×SSC, 0.1% SDS, once for 20 minutes at 65° C., with 1×SSC, 0.1% SDS, and twice for 20 minutes at 65° C., with 0.1×SSC, 0.1% SDS. Ten positive clones were found, and sequenced automatically, using T7 and SP6 primers for the pcDNA I/Amp vector, and the pCEP-4 forward primer for pCEP-4. Several MAGE-10 clones were isolated, and fell into two categories (2.5 kb, and 1.5 kb, respectively), with different 3'-ends. The difference may result from alternate oligo (dT) priming during the cDNA synthesis for the library. The clones all seemed to be identical but for the first 50–70 nucleotides at the 5'-end. Comparison to the known, genomic sequence delineated existence of at least four exons, the last two being identical to those predicted by DePlaen, et al. supra (positions 1740–1814, and 1890-end). The second exon corresponded to positions 603–701, while the first exon did not appear to correspond to any previously recognized MAGE-10 sequence. The open reading frame was found in the last exon. A sequence is set forth at SEQ ID NO: 3. The first 100 bases or so indicate consensus sequences, based upon the collective sequence information secured via these experiments. When this sequence was compared to other members of the MAGE family, nucleotides 471–530 of SEQ ID NO: 3 were identified as a stretch unique to MAGE-10. Identification of this portion of the sequence set out in SEQ ID NO: 3 characterizes MAGE-10.

EXAMPLE 10

Three clones were isolated from the pcDNAI/Amp library, described supra, and were used for in vitro transcription and translation. These inserts were about 1.5 kilobases long, terminating at about position 3156, using genomic sequence enumeration. One ug of each DNA was translated, using a commercially available system, and a luciferase control plasmid was used as control. Translation products were subjected to PAGE analysis, and duplicate gels of non-radioactively labeled product were transferred to membranes, where Western Blotting was carried out, using mAb 6C1, or polyclonal antibodies prepared as described infra. Radiolabelled materials showed a 72 kilodalton protein from all three clones tested, suggesting that the mAb was cross reactive with MAGE-1 and MAGE-10.

EXAMPLE 11

A study was carried out to determine if MAGE-10 was expressed in tumors and, if so, in what tumors.

To carry out these experiments, tumor samples were snap frozen at −80° C., total RNA 15was purified, and cDNA synthesis was carried out, in accordance with Weynants, et al., Int. J. Canc. 56: 826–829 (1994), the disclosure of which is incorporated by reference.

Following this, 1/40 of cDNA produced from 2 μg of total RNA was combined with 2.5 μl of PCR buffer (500 mM KCl, 15 mM MgCl$_2$, 100 mM Tris-HCl, pH 8.3), 0.25 μl of each dNTP (10 mM), 10 pmols of primers:

5'-CACAGAGCAG CACTGAAGGA G-3'

5'-CTGGGTAAAG ACTCACTGTC TGG-3'

0.625 units of Taq polymerase, and water to a final volume of 25 μl. The mixture was heated to 94° C. for 4 minutes, then PCR was carried out for 30 cycles (1 cycle: 1 minute at 94° C., one minute at 65° C., one minute at 72° C.), followed by a final extension step of 15 minutes at 72° C. The primers are located at nucleotides 264–283 and 726–748 of SEQ ID NO: 3, respectively.

Following the PCR amplification, samples (10 μl) of each reaction were size fractionated on 1.3% agarose gel containing ethidium bromide, and PCR products were visualized using ultraviolet trans-illumination.

If MAGE-10 was present, the primers should have yielded a 485 base pair product following amplification.

The results follow:

| | Proportion of tumors expressing gene MAGE-10 | |
|---|---|---|
| Bladder carcinomas | 5 of 15 | 33% |
| Superficial | 5 of 15 | 33% |
| Infiltrating | | |
| Brain tumors | 0 of 9 | |
| Breast carcinomas | 0 of 20 | |
| Colorectal carcinomas | 0 of 20 | |
| Esophageal squamous carcinomas | 6 of 15 | 40% |
| Head and neck squamous carcinomas | 7 of 20 | 35% |
| Leukemias | 0 of 25 | |
| Lung carcinomas | 6 of 15 | 40% |
| Adenocarcinomas | 10 of 20 | 50% |
| Squamous carcinomas | | |
| Melanomas (of cutaneous origin) | 4 of 19 | 21% |
| Primary lesions | 21 of 45 | 47% |
| Metastases | | |
| Mesotheliomas | 0 of 4 | |
| Myelomas | 3 of 15 | 20% |
| Neuroblastomas | 2 of 2 | |
| Prostatic carcinomas | 1 of 10 | 10% |
| Renal carcinomas | 0 of 20 | |

-continued

| | Proportion of tumors expressing gene MAGE-10 | |
|---|---|---|
| Sarcomas | 1 of 15 | 7% |
| Thyroid carcinomas | 0 of 5 | |
| Uterine carcinomas | 0 of 5 | |

EXAMPLE 12

Polyclonal antiserum against MAGE-10 was made as follows.

Immunogenic, MAGE-10 derived peptide (H)QDIIIATTDDTTAMASASSSATGSFSYPE (OH)

(SEQ ID NO: 4), a portion of the deduced amino acid sequence of MAGE-10 was made, as were hybrids of this peptide and helper peptide P-30.

Helper Peptide P30 is well known, as per Valmori, et al., J. Immunol. 149: 717–721 (1992). It is a tetanus toxin T cell epitope, with amino acid sequence:

FNNFTVSFWLRVPKVSASHLE (SEQ ID NO: 5). Peptides were dissolved at 400 ug/ml in 100 mM Tris-HCl, pH 7.5, 0.9% NaCl. A rabbit was immunized over a 56 day period, with hybrid peptide (0.5 ml) at day 0, the MAGE-10 peptide (0.5 ml) at day 14, a second 0.5 ml injection of hybrid at day 28, and a final injection at day 56, of 0.5 ml of the MAGE-10 peptide.

Antiserum produced in accordance with this protocol was tested for reactivity with MAGE-10 in various assays. Specifically, the in vitro translation product of expression of cDNA corresponding to SEQ ID NO: 3 was tested in Western blotting experiments, along the lines set forth supra. The antiserum was found to bind to a protein which was produced via the in vitro expression. It also recognized a 72 kDa band from melanoma lysates. In an ELISA, the polyclonal antibodies were found to recognize the MAGE-10 peptide.

The invention thus relates to MAGE-10 binding monoclonal antibodies and the hybridomas which produce them. The mAbs were found to be useful in determining expression of MAGE-10. The mAbs can be added, e.g., in labeled form, bound to a solid phase, or otherwise treated to increase the sensitivity of MAGE-10 detection. Any of the standard types of immunoassays, including ELISAs, RIAs, competitive assays, agglutination assays, and all others are encompassed with respect to the way the mAbs can be used. The detection of MAGE-10 expression product is useful, e.g., in diagnosing or monitoring the presence or progression of a cancer.

The isolated, MAGE-10 protein is also a feature of this invention. This molecule has a molecular weight of about 72 kDa as determined by SDS-PAGE, and is useful as an immunogen as is the peptide of SEQ ID NO: 4, shown by the examples to be immunogenic. Preferably, these are used in combination with a suitable adjuvant.

Isolated cDNA encoding MAGE-10 is also a feature of this invention, such as the cDNA of SEQ ID NO: 3. Also a part of the invention are cDNA molecules which have complementary sequences that hybridizes to SEQ ID NO: 3 under stringent conditions (e.g., 0.2×SSC, 0.1% SDS at 65° C. or, more preferably, 0.1×SSC). These should include, as a minimum, nucleotides 164–574 of SEQ ID NO: 3, in 5' to 3' order. Nucleic acid molecules consisting of nucleotides 164–185, and 553–574 of SEQ ID NO: 3 are especially useful as probes and/or primers, and are also a part of this invention. The sequences can be used in the form of expression vectors when operably linked to promoters, and then used to transform or transfect cells, to produce various recombinant eukaryotic cell lines and prokaryotic cell strains. Similarly, the sequences, and sequences such as those described supra can be used in various hybridization assays, such as PCR based assays. These are well known to the skilled artisan, and need not be repeated here.

Also a part of the invention are methods for determining expression of MAGE-10 in a sample. Such methods include various oligonucleotide hybridization assays, such as polymerase chain reaction (PCR), Northern Blotting, Southern blotting, etc. All of these assays involve the use of oligonucleotide molecules which hybridize to MAGE-10 DNA or mRNA, such as oligonucleotides comprising nucleotides 246–283, or 726–748, or 164–185, or 553–574 of SEQ ID NO: 3. Also a part of the invention are those oligonucleotides which, while not precisely complementary to the target molecule, i.e., a MAGE-10 coding sequence, are sufficiently complementary to hybridize thereto. The art is familiar with the design of such molecules. For example, it is well known that when RT-PCR is carried out, printers are generally 18–23 nucleotides long with the 6–8 nucleotides at the 3' end being essentially 100% complementary to target, with the remainder of the molecule permitting a great deal of mismatch. For Northern and Southern hybridizations, oligonucleotides at least 25–30 nucleotides long are preferred, which are at least 80% homologous to a strand of the nucleic acid molecules they are intended to hybridize to.

These assays have various uses. In addition to determining expression of MAGE-10, one can monitor situations where a patient is receiving therapy for a condition associated with expression of MAGE-10, such as cancer. For example, if a tumor has regressed and then reappears or metastasizes, one can determine this. In situations where therapies are based on inhibiting MAGE-10, such as antisense therapies, where cells respond by downregulating MAGE-10, and thus escape the therapeutic agent.

Also a part of the invention are antisense molecules, i.e., oligonucleotides which hybridize to the coding strand of MAGE-10 and inhibit transcription thereof. Preferably, such molecules are at least 7, preferably 20–30 nucleotides in length. Such molecules may be completely, or partially complementary to a MAGE-10 gene, as long as they can hybridize to the gene under standard physiological conditions. The art is fully familiar with such sequences and how to make these.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A method for determining if cancer cells which express MAGE-10 are present in a sample, comprising contacting said sample with at least one oligonucleotide molecule which specifically hybridizes to a nucleic acid molecule which encodes tumor rejection precursor MAGE-10, wherein hybridization of said at least one oligonucleotide molecule to a nucleic acid molecule is indicative of cancer cells which express MAGE-10 in said sample.

2. The method of claim 1, wherein said oligonucleotide molecule consists of nucleotides 264–283 of SEQ ID NO: 3, or nucleotides 726–748 of SEQ ID NO: 3.

3. The method of claim 1, comprising contacting said sample with an oligonucleotide molecule which comprises nucleotides 264–283 of SEQ ID NO: 3 and an oligonucleotide molecule which comprises nucleotides 726–748 of SEQ ID NO: 3.

4. The method of claim 1, wherein said cancer is bladder cancer, esophageal cancer, head and neck cancer, myeloma or prostate cancer.

5. The method of claim 1, wherein said oligonucleotide comprises at least nucleotides 264–283 or nucleotides 726–748 of SEQ ID NO: 3.

6. The method of claim 1, wherein said oligonucleotide comprises at least nucleotides 164–185 of SEQ ID NO: 3 or nucleotides 553–574 of SEQ ID NO: 3.

7. An oligonucleotide consisting of nucleotides 164–185 of SEQ ID NO: 3 or nucleotides 553–574 of SEQ ID NO: 3.

8. An isolated nucleic acid molecule consisting of nucleotides 471–530 of SEQ ID NO: 3.

9. A kit useful in determining expression of MAGE-10, comprising two different olegonucleotides, each of which consists of a nucleotide sequence selected from the group consisting of:
(i) nucleotides 264–283 of SEQ ID NO: 3,
(ii) nucleotides 726–748 of SEQ ID NO: 3,
(iii) nucleotides 164–185 of SEQ ID NO: 3, and
(iv) nucleotides 553–574 of SEQ ID NO: 3.

* * * * *

UNITED STATES PATENT AND TRADEMARK OFFICE
CERTIFICATE OF CORRECTION

PATENT NO.   : 6,221,593 B1            Page 1 of 1
DATED        : April 24, 2001
INVENTOR(S)  : Boon-Falleur et al.

It is certified that error appears in the above-identified patent and that said Letters Patent is hereby corrected as shown below:

Title page,
U.S. Patent Documents,
Change "3/1997" to -- 6/1994 --.

Title page,
Foreign Patent Documents,
Change "1994" to -- 1995 --.

Column 1,
Line 53, change "tum" to -- tum --.
Line 58, change "tum" to -- tum --.

Column 2,
Line 7-8, delete space on line 7 and line 8
Line 59, change "tum" to -- tum --.
Line 67, change "tum" to -- tum --.

Column 3,
Line 11, change "tum" to -- tum --

Column 6,
Line 39, after "mRNA" delete -- 15i --.

Signed and Sealed this

Thirtieth Day of October, 2001

Attest:

*Nicholas P. Godici*

NICHOLAS P. GODICI
*Attesting Officer*   *Acting Director of the United States Patent and Trademark Office*